(12) United States Patent
Nielsen et al.

(10) Patent No.: US 9,063,034 B1
(45) Date of Patent: Jun. 23, 2015

(54) **DETERMINATION OF THE ABSENCE OR PRESENCE OF *BACILLUS CEREUS* ENTEROTOXIN VIA A WESTERN BLOT**

(71) Applicant: Scientific Protein Laboratories, LLC, Waunakee, WI (US)

(72) Inventors: Dustin Nielsen, Poynette, WI (US); Rachel Wezeman, Middleton, WI (US); Matthew Bristol, Sun Prairie, WI (US); Mark Eifler, Madison, WI (US); Lisa Petersen, Lodi, WI (US); Erik Walke, Deforest, WI (US); Lin Rao, Madison, WI (US)

(73) Assignee: Scientific Protein Laboratories, LLC, Waunakee, WI (US)

( * ) Notice: Subject to any disclaimer, the term of this patent is extended or adjusted under 35 U.S.C. 154(b) by 72 days.

(21) Appl. No.: 13/654,222

(22) Filed: Oct. 17, 2012

Related U.S. Application Data

(60) Provisional application No. 61/547,999, filed on Oct. 17, 2011.

(51) Int. Cl.
  *G01N 33/573* (2006.01)
  *G01N 1/00* (2006.01)
(52) U.S. Cl.
  CPC ............ *G01N 1/00* (2013.01); *A61K 2121/00* (2013.01); *C12Q 2304/00* (2013.01); *G01N 2333/994* (2013.01); *G01N 2333/32* (2013.01); *G01N 2333/195* (2013.01)
(58) Field of Classification Search
  None
  See application file for complete search history.

(56) References Cited

U.S. PATENT DOCUMENTS 5,763,226 A * 6/1998 Wong et al. ................. 435/71.3

FOREIGN PATENT DOCUMENTS

WO    WO 2005012911 A1 * 2/2005

OTHER PUBLICATIONS

Beecher et al. 1990 (A novel bicomponent hemolysin from *Bacillus cereus*, Infection and Immunity, July: 2220-2227).*
Dietrich et al 2005 (Production and characterization of antibodies against each of the three subunits of the *Bacillus cereus* non-hemolytic enterotoxin complex, Appl. Env. Microb. 71(12): 8214-8220).*
Mamone et al. 2009 (Analysis of food proteins and peptides by mass spectrometry-based techniques, Journal of Chromatography A, 1216:7130-7142).*
MacPhee et al. 2010 (Methodological considerations for improving Western blot analysis, Journal of Pharmacological and Toxicological Methods, 61:171-177).*
Carroccio et al. 2001 (Efficacy of oral pancreatic enzyme therapy for the treatment of fat malabsoption in HIV-infected patients; Aliment Pharmacol. Ther. 15:1619-1625).*
Rowan et al. 1998 (Growth and enterotoxin production by diarrhoeagenic *Bacillus cereus* in dietary supplements prepared for hospitalized HIV patients; Journal of Hospital Infection 38: 139-146).*

* cited by examiner

*Primary Examiner* — Gary Nickol
*Assistant Examiner* — Mary Lyons
(74) *Attorney, Agent, or Firm* — Reinhart Boerner Van Deuren s.c.

(57) ABSTRACT

Disclosed is a method for the determination of the absence or presence of *bacillus cereus* enterotoxin in a protein sample via a western blot.

10 Claims, 1 Drawing Sheet

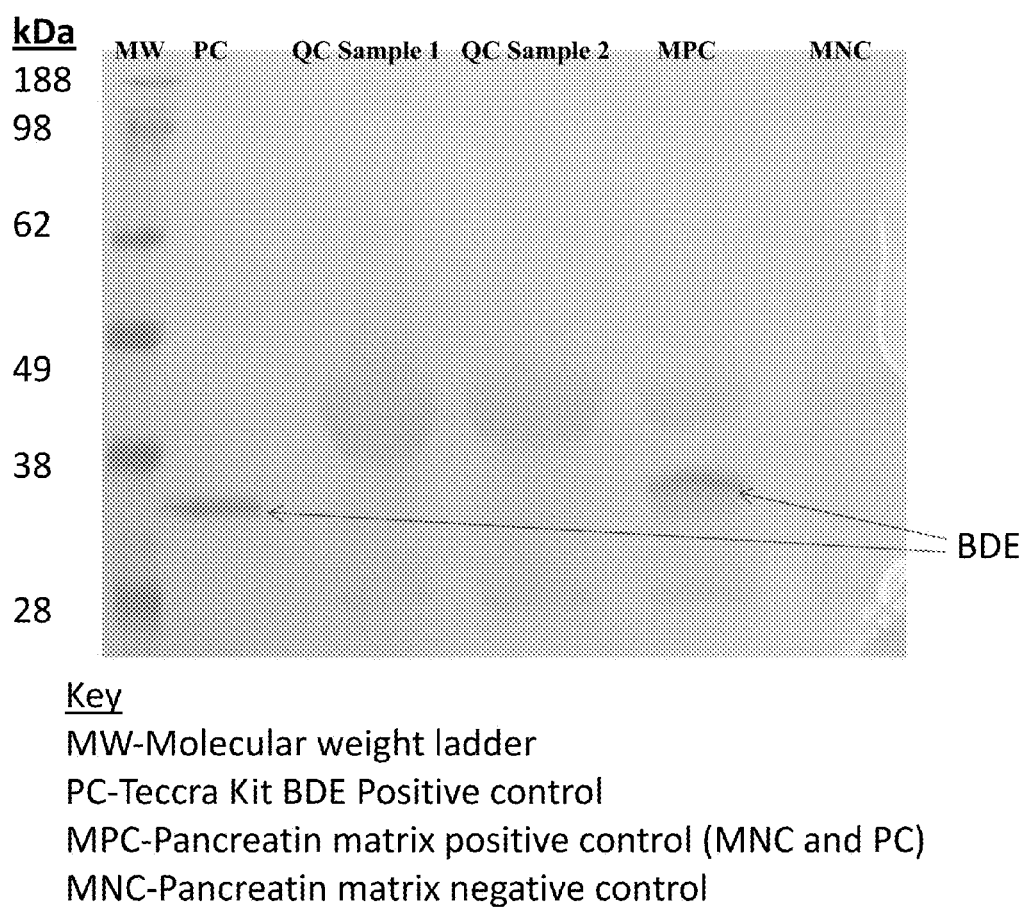
Key
MW-Molecular weight ladder
PC-Teccra Kit BDE Positive control
MPC-Pancreatin matrix positive control (MNC and PC)
MNC-Pancreatin matrix negative control

DETERMINATION OF THE ABSENCE OR PRESENCE OF *BACILLUS CEREUS* ENTEROTOXIN VIA A WESTERN BLOT This application claims priority benefit from provisional application Ser. No. 61/547,999 filed Oct. 17, 2011—the entirety of which is incorporated herein by reference.

FIELD OF THE INVENTION

The present invention relates generally to a method for determining the absence or presence of *Bacillus cereus* enterotoxin in a protein sample by employing a Western Blot method.

BACKGROUND OF THE INVENTION

*Bacillus cereus* is a gram-positive, rod-shaped, beta-hemolytic bacterium. It occurs widely in nature, being found in soil and in food, and is known to be a food-borne human pathogen causing emesis or diarrhea. The toxin produced by *Bacillus cereus* is known as *Bacillus* Diarrheal Enterotoxin (BDE), a three-component cytotoxin consisting of Hemolysin BL (Hbl), Nonhemolytic Enterotoxin (Nhe) and Cytotoxin K (CytK). Nhe is one of the major causes of non-hemolytic food poisoning.

The pancreas gland in mammals secretes a variety of enzymes and variety of substances, including proteases such as trypsinogen, chymotyrpsinogen, elastase and carboxypeptidase, peroxidase, pancreatic lipase, and amylase. Without these enzymes (normally produced by the human pancreas), a substantial portion of undigested food simply passes through the digestive tract and provides no nutritional benefit. The pancreatin/pancrelipase active pharmaceutical ingredient (API) is an enzymatically active product derived from porcine pancreas glands. Porcine pancreatin juice is closest to that of humans, with high proportions of lipase and alpha-amylase in comparison to other mammals. Therefore, pancreatin/pancrelipase is made from the pancreas of pigs, and is used to treat conditions in which pancreatic secretions are deficient, such as surgical pancreatectomy, pancreatitis and cystic fibrosis. It has been claimed that pancreatin is beneficial in the treatment of food allergies, celiac disease, autoimmune disease, cancer and weight loss. Pancreatin is sometimes called "pancreatic acid", although it is neither a single chemical nor an acid.

Pancreatin enzyme products (PEPs) of porcine or bovine origin have been available in the United States for the treatment of exocrine pancreatic insufficiency (EPI) since before the enactment of the Federal Food, Drug, and Cosmetic Act of 1938 (the Act). With the exception of one PEP approved in 1996, the products have been marketed without New Drug Applications (NDAs) and were considered as dietary supplements. In both Europe and the US, the use of PEPs has been severely restricted in recent years, due to concerns about the products' origin from animal tissue (with concomitant risk of viral disease transmission) and the relatively poor characterization and lack of standardization of enzymatic bioavailability in humans. The Food and Drug Administration (FDA) determined that an Over The Counter (OTC) monograph would not be sufficient to adequately regulate these drug products or to standardize enzyme bioactivity, safety and effectiveness. The FDA's guidance for the industry requires all pharmaceutical companies marketing pancreatic enzymes for pancreatin deficiency to be approved under New Drug Applications. Since April 2010, PEPs are only available by prescription and only PEPs approved by the FDA remain on the market.

To be approved, an NDA must meet the requirements in 21 CFR §314.50 regarding chemistry, manufacturing and controls (CMC) information. The drug substance should be adequately characterized using chemical, physical and biological testing methods. Batch-to-batch consistency with respect to chemical identity, biological activity of different classes of enzymes including specific activity, and identity and purity levels should be demonstrated. Since Pancreatin is referenced in a new NDA, the agency expects the pancreatin Drug Master File (DMF) to meet current ICH Q6B requirements for specifications. Specifications for the drug substance should include tests for identity, biological activity of different classes of enzyme, purity and other relevant attributes. Because of the complexity of pancreatin extract product, it is unlikely that currently-available physiological and biological analytical tools would be able to demonstrate that the active ingredients in pancreatic extract products from two different batches/manufacturers are the same. Current United States Pharmacopeia (USP) monograph tests are insufficient to characterize the API to meet the ICH guideline. The new regulatory guidelines now require better methods to characterize pancreatin API.

3M's TECRA® Assay is an enzyme-linked immunosorbent assay (ELISA) normally used for determining the absence or presence of bacterial toxins from organisms such as *Bacillus cereus* in food and food-related products. It can, with some difficulty, be modified and adapted to test more complex biologically-derived products such as pancreatin for the absence or presence of BDE. Even when so modified and adapted it remains prone to false positive and false negative results. When the TECRA® assay is used for the testing of complex protein-dense mixtures such as pancreatin, non-specific binding of its antibodies to porcine proteins is clearly evident and contributes to difficulties in its routine use.

Therefore, a more reliable assay is desired for determining the absence or presence of *Bacillus cereus* in a sample that minimizes or eliminates altogether the false positives and false negatives. The assay should be at least as sensitive as the TECRA® assay for the detection of BDE in a positive control sample.

SUMMARY OF THE INVENTION

In light of the foregoing, it is an object of the present invention to provide a method for the detection of at least one component of *Bacillus* Diarrheal Enterotoxin (BDE) in a sample by using a Western Blot procedure, thereby improving upon the prior art and/or overcoming various deficiencies or shortcomings thereof. The method includes the separation of at least one of the four enterotoxins of BDE from a protein sample by gel electrophoresis and then detecting or identifying the one or more enterotoxins by using at least one probe antibody specific for the enterotoxin.

Accordingly, it will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

Other objects, features, benefits and advantages of the present invention will be apparent from this summary and the following descriptions of certain embodiments, and will be readily apparent to those skilled in the art. Such objects, features, benefits and advantages will be apparent from the above as taken into conjunction with the accompanying examples, data, and all reasonable inferences to be drawn therefrom.

BRIEF DESCRIPTION OF THE DRAWINGS

FIG. 1 is a *Bacillus* Diarrheal Enterotoxin Western Blot for QC Sample 1 (pancreatin sample) and QC Sample 2 (pancreatin sample).

DETAILED DESCRIPTION OF THE INVENTION

Accordingly, the present invention provides a Western Blot method to identify one, two, three or all four of the enterotoxins (components) of BDE in a sample, the method comprising separating at least one of the four components of BDE from the sample by sodium dodecyl sulfate polyacrylamide gel electrophoresis (SDS-PAGE) and then identifying the one or more components by using at least one probe antibody specific for the at least one component. Specifically, the four components of BDE are Hemolysin BL (Hbl), Nonhemolytic Enterotoxin (Nhe), Cytotoxin K (CytK) and Enterotoxin T (BcET). Hbl is composed of three subunits, namely a 37 KDa (B), a 38 KDa ($L_1$) and a 46 KDa ($L_2$) subunit. Nhe is also composed of three subunits, namely a 39 Kda (NheB), a 45 KDa (NheA) and a 105 KDa (NheC) subunit. CytK is composed of one 37 KDa unit. BcET is composed of one 41 KDa unit. The method of the invention can be used to separate one or more of the subunits of each component of BDE to detect the presence of BDE.

Illustrating certain non-limiting aspects and embodiments of the invention, a Western Blot procedure is used to determine the absence or presence of a component or components of BDE, or a subunit of a component, in a sample, such as, for example, a sample of pancreatin. Because of the ability of antibody molecules to recognize and bind to antigen very specifically, this antibody-binding specificity is used to identify one or more of Nhe, Hbl, BcET and CytK, or any subunits thereof.

In a typical Western Blot procedure, one or more of Nhe, Hbl, BcET and CytK, or one or more subunits thereof, are separated from a sample of, for example, pancreatin active pharmaceutical ingredient (API) on a denaturing sodium dodecyl sulfate (SDS) polyacrylamide gel and are transferred (blotted) to a nitrocellulose membrane. The membrane is then exposed sequentially to solutions containing primary antibody, followed optionally by a secondary antibody coupled to a reporter enzyme. The membrane is then soaked in a substrate solution reactive with the reporter enzyme and a colored reaction takes place, which results in identifying the antigen as a band.

In an embodiment of the invention, sample preparation begins with adding a sample buffer, such as for example, Tris-Glycine SDS sample buffer, and additional SDS to each sample tube, including to a matrix positive control (MPC) tube and a blank positive control (BPC) tube. Other suitable buffers include, but are not limited to, Bis-Tris buffer, MOPS buffer and MES buffer. Typically, the ratio of SDS to sample protein in the method of the invention is approximately 1.4:1. Each sample tube is then pre-heated. It is noted that the temperature and time of the pre-heating step is important. In a preferred embodiment, pre-heating is done at a temperature near the boiling point of water for a period of time around 5 minutes. A BDE spiking solution of desirable concentration using an appropriate dilution of BDE supernatant with purified water (PW) is prepared. The supernatant starting concentration is based on a standardization. As described herein, PW is water that meets or exceeds the quality requirements in the USP Purified Water monograph and is processed by a validated, controlled system. The BDE spiking solution is then added to the MPC and BPC. Immediately following the BDE spiking step, between 0.5-3 mg, preferably 1-2 mg, sample protein is added to each sample tube. Subsequent to the dissolution of each protein sample, the tubes are centrifuged.

The samples are then loaded and the PAGE is run at a constant voltage for a certain period of time. High voltage, long running times and cold transfer buffer are not necessary. Suitable SDS-polyacrylamide gels for use in the invention include, but are not limited to, Bis-Tris and Tris-Glycine.

The gel is then transferred to a membrane, such as, for example, a nitrocellulose membrane. The nitrocellulose membrane is subsequently washed, treated with a blocking solution and incubated for a period of time. After decanting the blocking solution, an anti-BDE antibody solution is applied to the membrane, followed by incubation in a refrigerator. The antibody solution is then decanted and the membrane is washed several times with one or more buffers. The membrane is then allowed to develop. Both the BPC and MPC lanes must be positive for the detection of BDE. NheA, a subunit of Nhe, has a molecular weight around 40-45 KDA and PI around 5.2.

In an embodiment of the invention, a suitable primary antibody for use in the method is one that, for example, conjugates to protein A horseradish peroxidase (HRP) to produce a signal, such as, for example, the antibody included in the TECRA® kit. Optionally, a secondary and even tertiary antibody can be used in the method of the invention. The optional secondary antibody is one that can be alkaline phosphatase conjugated rather than HPR conjugated.

In yet another embodiment of the invention, the development and detection of BDE through its conjugation to HRP is performed by staining the membrane with stains that detect HRP, such as, for example, chloronapthol and diaminobenzidine (collectively, CN/DAB). Optionally, stains such as nitroblue tetrazolium and 5-bromo-4-chloro-3'-indolphosphate can be used to detect alkaline phosphatase conjugated BDE. It is understood by those skilled in the art that other detection methods can be used either alone or in combination with other detection methods. Such methods include, but are not limited to, chemiluminescence.

EXAMPLES

Reagents

1) Antibody conjugate; 2) BDE supernatant; bovine serum albumin, powder (BSA); 3) blank positive control (BPC); 4) CN/DAB substrate kits (10× substrate, 1× buffer); 5) matrix negative control (MNC); 6) matrix positive control (MPC); 7) methanol, USP grade; 8) molecular weight standard (MW); 9) nitrocellulose membranes; 10) normal rabbit serum (NRS); 11) pancreatin matrix negative control (MNC); 12) signal enhancement reagents; 13) sodium dodecyl sulfate (SDS), powder; 14) TECRA® wash solution concentrate; 15) Tris-Glycine precast gels (10%, 1.5 mm×10 wells); 16) Tris-Glycine SDS running buffer (10×); 17) Tris-Glycine SDS sample buffer (2×); 18) Tris-Glycine SDS transfer buffer (25×); 19) Tween 20.

Example 1

Reagent Preparation

A) Preparation of 20% SDS—20.0±0.1 g SDS powder is dissolved in 100 mL PW. The solution is stored at room temperature for one year.

B) Preparation of BDE antibody solution—Antibody conjugate is reconstituted by adding one freshly-opened vial of antibody diluent to one freshly-opened vial of dried conjugate antibody per TECRA® Kit instructions. The mixture is stored in a refrigerator for 2 weeks.

C) Preparation of running buffer—500 mL of Tris-Glycine SDS running buffer (10×) is diluted to 5 L with PW. The solution is stored at room temperature for one year.

D) Preparation of 1× Tecra wash buffer (TWB):—1 bottle of TECRA® wash solution concentrate is diluted with 2 L of PW. The buffer is stored at room temperature for 2 months.

the water bath or heating block. It is noted that extended heating of the BDE without addition of pancreatin may adversely affect spike recovery, resulting in suitability failure. When all the pancreatin has been added to the tubes, vortexing and heating is continued to all tubes until the pancreatin dissolves. Finally, all tubes are removed from the heat and transferred to a centrifuge, wherein the tubes are centrifuged for 3 minutes at 13000 rpm.

The gel(s) are loaded according to that depicted in Table 1. It is noted that the sample order, and not the orientation, is important.

TABLE 1

| Well 1 | Well 2 | Well 3 | Well 4 | Well 5 | Well 6 | Well 7 | Well 8 | Well 9 | Well 10 |
|---|---|---|---|---|---|---|---|---|---|
| MW 10 µL | BPC 40 µL | Sample Buffer 2X 20 µL | Sample 1 40 µL | Sample Buffer 2X 20 µL | Sample 2/Buffer 2X (as needed) 40 µL/20 µL | Sample Buffer 2X 20 µL | MPC 40 µL | Sample Buffer 2X 20 µ | MNC 40 µL |

E) Preparation of transfer buffer (1.25×)—500 mL of Tris-Glycine SDS transfer buffer (25×) is diluted to 10 L with PW. The buffer is stored at room temperature for one year.

F) Preparation of 0.1% Tween solution—1 mL of Tween20 is added to 1 L of TWB. The mixture is stored in a refrigerator for one year.

Example 2

PAGE Setup

An electrophoresis box is assembled. Two samples per gel (10% Tris-Glycine precast, 1.5 mm×10 wells) can be analyzed. The comb and tape from the gel(s) is removed.

500 mL of running buffer is measured and used to fill the assembled gel box. The inner chamber is filled above the gel wells and the remainder is poured to the outer chamber.

Example 3

Sample Preparation

Microcentrifuge tubes are prepared. One tube is necessary for each of the three controls, i.e. matrix negative control (MNC), matrix positive control (MPC) and BDE positive control, and one tube for each sample to be tested.

500 µL of 2× Tris-Glycine SDS sample buffer and 470 µL of 20% SDS is pipetted to each tube. Then, 30 µL of PW is pipetted to each sample tube and the Matrix Negative Control (MNC) tube. The tubes are then capped and transferred to a water bath or heating block for pre-heating. The tubes are pre-heated at 95-100° C. for 5 minutes.

50±1 mg of pancreatin negative control is weighed for each of the matrix controls. 50±1 mg of pancreatin sample is weighed for each sample tube.

A BDE spiking solution of desirable concentration is prepared using an appropriate dilution of BDE supernatant with PW. The supernatant starting concentration is based on a standardization.

After the tubes are pre-heated, 30 µL of BDE spiking solution (35-45 ng/mL) is pipetted to the MPC and BPC tubes.

The pancreatin samples are then immediately added to the corresponding heated tubes, one tube at a time, i.e. the pancreatin is added, vortexed briefly, and the tube is returned to When loading is complete, the lid is attached to the electrophoresis box and the leads are connected to the power supply. The power supply is set to 175V, constant voltage.

The PAGE should run approximately 1 hour, 15 minutes. The 36 kDa marker (carbonic anhydrase, the blue band just above the red protein in the MW standard) enters into the $4^{th}$ quadrant before the run is stopped.

Example 4

Transfer 100 mL of methanol is added to 500 mL of transfer buffer. The solution is poured into a shallow pan. Several fiber pads and a nitrocellulose membrane are soaked therein. The membrane is soaked for 2 minutes before being assembled with the gel.

The cassette housing the gel is opened. The thicker "foot" at the bottom of the gel is trimmed and the wells at the top of the gel are cropped, leaving the bottom of the wells intact.

The pan of transfer solution is added. The transfer assembly, bottom to top, is as follows: 1) anode side of the transfer module (the trough-shaped portion); 2) two fiber pads; 3) blot paper; 4) gel; 5) nitrocellulose membrane; 6) blot paper; 7) fiber pads (to ~0.5 cm above the edge of the anode side of the transfer module); 8) cathode side of the transfer module.

Throughout the assembly, care is taken to avoid bubbles of air being trapped between the transfer layers. The transfer assembly is then moved to an electrophoresis box. A clamp is used to seal the inner chamber. The transfer solution is poured from the pan to the inner chamber and the contents of the chamber are fully submerged. The remainder of the transfer solution is poured into the outer chamber. The lid is attached to the electrophoresis box and the leads connected to the power supply. The power supply is set to 25V, constant voltage, and the transfer is started. The transfer is stopped after approximately 100±10 minutes.

Example 5

Signal Enhancement

The nitrocellulose membrane is moved from the transfer assembly to a wash box. A wash box is any vessel in which a nitrocellulose membrane can lie flat with some clearance on all four sides. Ideally, it has a lid, and 15 mL is a sufficient volume to submerge the membrane. The membrane is rinsed with PW. The liquids are not poured directly on the surface of the blot. 15 mL of signal enhancement reagent 1 is added and the contents are incubated for 2 minutes on a shaker. The membrane is then rinsed 5 times with PW and 15 mL of signal enhancement reagent 2 is added and the contents are incubated for 10 minutes on the shaker. Again, the membrane is rinsed 5 times with PW.

Example 6

Blocking

Blocking solution is prepared by dissolving 0.20±0.01 g of BSA in 20 mL of 0.1% Tween solution. 0.2 mL of NRS is pipetted to the solution. The resulting blocking solution is poured into the wash box with the membrane. The contents are incubated for 30-60 minutes on the shaker and the blocking solution is then decanted.

Example 7

Antibody Incubation 3.75 mL BDE antibody solution and 0.15 mL NRS is pipetted to 11.25 mL TWB. This solution is then poured into the wash box with the membrane and the contents are incubated for 12 hours in a refrigerator.

Example 8

Developing the Membrane

The antibody solution is decanted. The membrane is washed four times with TWB. For the final two washes, the wash box is placed on the shaker for approximately 5 minutes. 2 mL of 10× CN/DAB substrate concentrate is combined with 18 mL of stable peroxide buffer. Formation of off-white solid is sometimes observed. The resulting solution is filtered through a 1.2 μm filter. When the washes are complete, the TWB is decanted and the filtered CN/DAB solution is added to the wash box. The membrane(s) are allowed to develop until a band, similar to that which develops in the BPC lane, develops in the MPC lane in approximately 5-15 minutes. The reaction is stopped by washing the membrane with PW.

Interpreting the Membrane

For both sections below, a positive result for the presence of BDE is defined as the presence of a narrow band or closely defined doublet with a MW of ~42 kDa (NheA subunit of Nhe). The ladder is referenced in lane 1 to estimate MW. A negative result is defined as the absence of a discrete band in this region.

Section 1 (Assay Suitability): All of the following criteria described must be met. Absence of any one of these criteria results in the sample being invalidated.

A) All control lanes are interpretable. No bubble marks appear in the region where a BDE band might appear. The intensity of the background color does not interfere with recognition of a BDE result.

B) The MW ladder, as it appears on the membrane, has bands that bracket the BDE band (at least one higher, at least one lower).

C) The BPC lane is positive for BDE. The BDE band appears as a thin band or a closely resolved doublet between the third and fourth major MW ladder bands.

D) The MPC lane is positive for BDE. This band can appear at a slightly different apparent MW than in the BPC lane, and it is likely to be less intense and more diffuse.

E) The MNC lane is negative for BDE.

Section 2 (Sample Interpretation): Sample results are not valid and are not recorded if: i) the run fails any of the above system suitability criteria; ii) the sample lane is not interpretable. No bubble marks appear in the region where a BDE band appears. The intensity of the background color does not interfere with recognition of the BDE result.

If all suitability criteria are met, the result for each non-control sample tested is interpreted. The following is recorded: "pass" for any sample that appears negative for the presence of BDE; "fail" for any sample that appears positive for the presence of BDE. FIG. 1 represents BDE Western Blots for various samples of pancreatin. The samples are determined to be negative for the presence of a BDE component or subunits thereof. Referring to FIG. 1 and as defined herein, "PC" is a positive control in the absence of pancreatin matrix, provided by 3M TECRA® (suppliers of the kit); "MPC" is the positive control (PC) in the presence of pancreatin, wherein the pancreatin used as the matrix is a previously tested lot of pancreatin shown to be free of BDE; "MNC" is a previously tested lot of pancreatin shown to be free of BDE. FIG. 1 illustrates that a positive result for the presence of BDE is defined as the presence of a narrow band or closely defined doublet with a MW of ~42 kDA. A negative result is defined as the absence of a discrete band in this region. All control lanes are interpretable. The intensity of the background color does not interfere with recognition of a BDE result. The MPC lane is always positive for BDE, while the MNC lane is always negative for BDE.

The disclosures of all articles and references, including patents, are incorporated herein by reference. The invention and the manner and process of making and using it are now described in such full, clear, concise and exact terms as to enable any person skilled in the art to which it pertains, to make and use the same. All references cited in this specification are incorporated herein by reference. It is to be understood that the foregoing describes preferred embodiments of the present invention and that modifications may be made therein without departing from the spirit or scope of the present invention.

What is claimed is:

1. A method for determining the absence or presence of one or more components of *Bacillus* Diarrheal Enterotoxin (BDE) in a pancreatin Active Pharmaceutical Ingredient (API) sample comprising separating the one or more components of BDE from the pancreatin API sample by sodium dodecyl sulfate polyacrylamide gel electrophoresis (SDS-PAGE), and identifying one or more components of BDE by using at least one probe antibody specific for at least one or more components of BDE; wherein the one or more components of BDE are selected from the group consisting of Hemolysin BL (Hbl), Nonhemolytic Enterotoxin (Nhe), Cytotoxin K (CytK) and Enterotoxin T (BcET).

2. The method according to claim 1 wherein identifying the one or more components further comprises
    transferring the separated components to a nitrocellulose membrane and sequentially exposing the components to solutions containing primary antibodies, and
    soaking the membrane in a substrate solution to develop a colored reaction of the bound primary antibody to the component, resulting in identifying the component as a visible band on the membrane.

3. The method according to claim 2 wherein the one or more components is Nhe.

4. The method according to claim 3 wherein the Nhe component is represented by a NheA subunit.

5. The method according to claim 1 wherein the ratio of sodium dodecyl sulfate to pancreatin sample in the SDS-PAGE is about 1.4 to 1.

6. The method according to claim 2 wherein the SDS-PAGE is run with a matrix positive control and a blank positive control to determine the detection of BDE.

7. The method according to claim 1 wherein the SDS-PAGE is run on a Bis-Tris or Tris-Glycine SDS-polyacrylamide gel.

8. The method according to claim 2 wherein the components are exposed to solutions containing secondary antibodies after exposure to the primary antibodies.

9. The method according to claim 6 wherein the membrane is stained to detect the primary antibody bound component.

10. The method according to claim 9 wherein the stain is selected from the group consisting of chloronapthol and diaminobenzidine, nitro-blue tetrazolium and 5-bromo-4-chloro-3'-indolphosphate.

* * * * *